US005538740A

United States Patent [19]

Abad

[11] Patent Number: 5,538,740
[45] Date of Patent: Jul. 23, 1996

[54] THERAPEUTIC AND COSMETIC COMPOSITIONS FOR TREATMENT OF SKIN

[75] Inventor: Rafael Abad, Madrid, Spain

[73] Assignee: Atherton Investments, Ltd., Madrid, Spain

[21] Appl. No.: 230,009

[22] Filed: Apr. 19, 1994

Related U.S. Application Data

[63] Continuation of Ser. No. 837,830, Feb. 25, 1992, abandoned, which is a continuation-in-part of Ser. No. 756,167, Sep. 6, 1991, abandoned, which is a continuation-in-part of Ser. No. 663,257, Mar. 1, 1991, abandoned.

[51] Int. Cl.$^6$ ............................... A61K 35/62
[52] U.S. Cl. .................. 424/547; 424/405; 424/59; 424/65; 424/DIG. 13; 514/423; 514/419; 514/400; 514/556
[58] Field of Search ................... 424/547, 537, 424/538, 542, 547; 530/855–858

[56] References Cited

U.S. PATENT DOCUMENTS

| | | | |
|---|---|---|---|
| 2,686,144 | 8/1954 | Gonzalez | 167/65 |
| 3,885,012 | 5/1975 | Tschesche et al. | 424/177 |
| 3,899,006 | 6/1975 | Nagaszwa et al. | 426/656 |
| 4,134,885 | 1/1979 | Valjukas et al. | 260/112 B |
| 4,314,992 | 2/1982 | Bitakaramire | 424/88 |
| 4,393,045 | 7/1983 | Henderson et al. | 424/95 |
| 4,473,640 | 9/1984 | Combie et al. | 435/18 |
| 4,550,020 | 10/1985 | Rothman | 424/547 |
| 4,855,285 | 8/1989 | Stevens | 514/12 |
| 4,886,545 | 12/1989 | Peck et al. | 71/88 |
| 4,892,871 | 1/1990 | Nathanson | 514/227.2 |

FOREIGN PATENT DOCUMENTS

| | | |
|---|---|---|
| 501M | 9/1962 | France. |
| 1501 | 9/1962 | France. |
| 3664 | 11/1965 | France. |
| 3664M | 11/1965 | France. |
| 2146909 | 3/1973 | France. |
| 2595247 | 9/1987 | France. |
| 1813154 | 7/1970 | Germany ........................ 424/547 |
| 2318787 | 10/1974 | Germany. |
| 05936618 | 2/1984 | Japan. |
| 01207219 | 8/1989 | Japan. |

OTHER PUBLICATIONS

Treatment of Radiodermatitis and Burns, Memorandum of Investigation, Dr. Rafaed Abad, Mar. 1988.
Una Nueva Sustancia en el Tratamiento de los Radiodermitis, Especialmente de Enfermos Neoplasicos. Factores Radiobiologicos Y Terapeuticos, "Acta Oncologica", vol. V1, No. 1, 1967 and English translation.
Microbiology 2nd Ed., 1973.
Chemisches Zentralblatt, vol. 25; p. 9182 1962.
G. Brambilla et al. (last abstract).

*Primary Examiner*—Neil S. Levy
*Attorney, Agent, or Firm*—Margaret B. Kelley; Rogers and Wells

[57] ABSTRACT

An active ingredient for a therapeutic or cosmetic composition is obtained from live gastropoda (e.g., snails) which are physically stimulated (e.g., by centrifuging) to cause secretion of a fluid which is then centrifuged and filtered. Preferably the gastropoda are fasted prior to the physical stimulation. The therapeutic or cosmetic compositions contain about 0.1–30% of the active ingredient which is a mixture of amino acids and atoxic substances, an effective amount of an excipient preferred for use with biologically active ingredients, and other conventional ingredients provided they do not affect the stability and/or the activity. The therapeutic composition, in the form of a topical cream, can be used to treat various types of burns, dermatitis, eczema, diaper rash, and difficult to heal wounds. It can also be used to prevent skin cancer and radiodermatitis. The cosmetic composition can be used as hand and face creams, an anti-wrinkle cream, a sunscreen cream, a moisturizing lotion, and a deodorant.

16 Claims, No Drawings

THERAPEUTIC AND COSMETIC COMPOSITIONS FOR TREATMENT OF SKIN

This is a continuation of Ser. No. 837,830 filed Feb. 25, 1992, now abandoned, which is a continuation-in-part of Ser. No. 756,167 filed Sep. 6, 1991, now abandoned, which is a continuation-in-part of Ser. No. 663,257 filed Mar. 1, 1991, now abandoned.

BACKGROUND OF THE INVENTION

The present invention relates to an active ingredient obtained from a gastropod (e.g., a snail) for use in therapeutic and cosmetic compositions. The compositions are applied to the skin or various mucous membranes.

Products derived from snails have been used in various medical products and processes. β-Glucuronidase obtained from crop fluid of the snail *Helix pomatia* has found use in a method for detecting morphine and its analogues, as well as enzymatic studies involving the metabolism of steroids (see U.S. Pat. No. 4,473,640 issued to J. D. Combie et al.). A Fascioliasis vaccine, particularly for bovine administration, is prepared from *Lymnaea natalensis* (see U.S. Pat. No. 4,314,992 issued to P. K. Bitakaramire). A polysaccharide hydrolyzing enzyme produced by a snail is used to treat yeast cells so that the walls disintegrate (see U.S. Pat. No. 3,889,006 issued to T. Nagasawa et al). Serum proteins such as hemocyanin from the Keyhole limpet (a marine gastropod mollusk) have been used to modify the peptides administered to primate animals to control biological activity attributable to chorionic gonadotropin (see U.S. Pat. No. 4,855,285 issued to V. C. Stevens).

U.S. Pat. No. 3,8815,012 (issued to Tschesche et al.) discloses the preparation of a protease-inhibiting substance (an iso-inhibitor) from homogenized edible snails of the genus *Helix* and family *Helicidae* (e.g., *Helix pomatia*).

The iso-inhibitor of the '012 patent is a chemically treated product derived from dead edible snails from a specific genus and family. The homogenized mixture used to produce the iso-inhibitors contains the blood, muscle, kidney, lung, and excrement of the edible snail. With a dead animal, such as the frozen and shelled snails used in the '012 composition, the starting product derived contains the product from the last biological reaction of that animal. Also, the product may contain toxic substances from the snail muscle and pathogenic viruses from the excrement.

The iso-inhibitors are prepared by: (a) homogenizing (i.e., crushing) the shelled frozen snails; (b) separating the resulting homogenate into a precipitate and a supernatant liquid (generally the separation is carried out by centrifuging at about 12,000 rpm (24,000 G) for 60 minutes); (c) mixing the supernatant liquid with ammonium sulfate up to 63% of the saturation concentration to precipitate the protease—inhibiting substance; and (d) optionally fractionating the substance by gel fractionation and selecting the most active fraction(s) or optionally fractionating the substance on a cation exchange resin to obtain a plurality of fractions containing a different iso-inhibitor.

The medical indications for the '012 composition are negative and diverse. They include injectable aqueous solutions containing the iso-inhibitors for use in the treatment of thrombotic or hemorrhagic conditions including acute pancreatitis, obstructive thrombus, nasal plugging, stopping bleeding in the sinus maxillas, esophagus varices in cirrhosis of the liver, and uterus carcinoma. One of the three prophylactic haemostyptic uses suggested is reduction of radiation damage in irradiation of malignant growths (i.e., cancer tumors).

Radiodermatitis (i.e., dermatitis resulting from overexposure to sources of radiant energy such as x-rays, gamma radiation or like radiation) is one of the most annoying complications in the treatment of neoplastic diseases and can lead to the suspension of treatment. It is also the feared occupational disease of medical practitioners who carry out the radiation treatments and of people working in nuclear plants. One of the most serious threats is the possible development of cancer from such exposure. Burns of all types are also one of the most difficult conditions to treat.

Treatments for radiodermatitis are discussed in the article "A New Substance In The Treatment Of Radiodermatitis, Particularly of Neoplastic Patients. Radiobiological and Therapeutic Factors" by Dr. Rafael Abad, Acta Oncological, VI, No. 1 (January–June 1967). The treatments include surgical treatments, physical treatments such as the use of ultraviolet, infrared, and red spectrum rays, ultrasonics, diathermy, and radar, and pharmacological treatments using inorganic, organic or biological products.

The physical treatments have little value except as a supplement to another primary therapy and are not recommended for cases occurring in an area with neoplastic processes. The danger of necrosis must be seriously considered before any physical treatments are employed. Infrared and red spectrum rays are not used because they increase erythema. Ultraviolet radiation was commonly used but is no longer used, even though it can lower pain at the lowest doses, because it has no prophylactic effect. The use of radar as an anti-inflammatory agent at very weak doses is effective; however, it can cause vascular complications like permeability and sweating.

Many pharmacological treatments have been tried. These include oral administration of large amounts of potassium iodide, local administration of acidified hydrogen peroxide to form nascent iodine in situ, and topical treatments with paraffin, zinc stearate, zinc oxide, animal fats (e.g., lanolin), petroleum jelly, and salves containing the juice of the aloe vera plant. These treatments are non-specific and most act as a mere excipient. Topical treatments often include anesthetics to relieve the pain, antihistamines to relieve the itch and redness, and vegetable materials such as chlorophyll. Other ingredients are used to increase penetration by means of hyaluronidase. Vitamin H, Vitamins A and D (halibut ointment), and pantothenic acid alone or mixed in a lyophilized mixture with trypsin have also been used although they are not curative. Sulfide-containing amino acids are important as radioprotectors and regenerators of radiolesions. Cysteine and methionine have been used both internally and topically. Various hormones have been used, including insulin, adrenalin, thyroid, female hormones, and heparin (topically). The use of insulin and adrenalin as radioprotectors is undesirable since they increase sensitivity. The use of cortisone (both topically and internally) is important. Substances such as nitrogenated mustards and chloroquine have also been used unsuccessfully.

The treatment of burns produced by ionizing radiations, chemical agents (e.g., mustard gas or similar agents used in chemical warfare), and thermal agents presents similar problems. The products used to treat the burns are non-specific and most act as mere excipients. They include blastostimulins, chymotrypsin, trypsin, cortisone, pantothenic acid, and vitamins.

Ionizing radiation is more likely to cause more devitalization, whereas thermal and chemical burns are more likely to cause necrosis. Repeated exposure to ultraviolet radiation is more likely to cause cancer (similar to the cancers caused by low and repeated doses of ionizing radiation). With all types of burns, skin or mucous cancer can develop.

The above treatments have not, however, been satisfactory. There is therefore a need for an effective therapeutic composition, particularly a composition which decreases local reactivity and protects the skin or mucous membrane, mitigates pain, favors tissue regeneration, eliminates cellular detritus, and prevents infection. Specifically, there is a need for a therapeutic composition which is both a radioprotector (i.e., it protects against radiodermatitis) and a restorative. There is also a need for a therapeutic composition which is effective in the treatment of other types of burns, particularly injuries to skin and mucous membranes caused by exposure to chemical agents, and which can prevent skin cancer due to exposure to ultraviolet light. There is also a need for a composition for use in the treatment of abrasions, rashes, wounds, varicose ulcers and the like. There is also a need for a composition for use in the treatment of wrinkled skin or skin with stretch marks.

Many cosmetic treatments have been tried. These include treatments with vitamins, embryonic, and placental extracts which either place water or lipids on the skin.

The above treatments have not been satisfactory. There is therefore a need for a regenerative treatment that acts as a biological coating.

SUMMARY OF THE INVENTION

The present invention provides a composition (hereafter referred to as the active ingredient) for use in therapeutic and cosmetic compositions, typically creams. The therapeutic compositions can be used to prevent radiodermatitis and sunburns; to treat abrasions, chafing, chapping, itching, diaper rash, eczema, dermatitis, and radiodermatitis; and to heal abrasions, burns (including radiation, chemical, and thermal burns), slow healing wounds, and ulcers. The cosmetic compositions can be used to nourish the skin and treat wrinkles and stretch marks on the skin. The present invention also provides a method for obtaining the active ingredient and for preparing the therapeutic and cosmetic compositions containing the active ingredient.

The active ingredient consists essentially of a secretion from a physically stimulated live gastropod. The secretion is a mixture of glandular secretions from the mucinous, albuminous, and salivary glands. Each secretion is responsible for certain therapeutic effects. The secretion from the mucinous or mucous gland, located in the foot of the gastropod, has a curative and restorative effect. The secretion from the albuminous (proteic) gland, located inside the body of the gastropod, provides an antibiotic effect in addition to curative and restorative effects. The secretion from the salivary gland, present in the digestive system of the gastropod, provides a digestive and penetrating effect which is responsible for the digestion of the dead cells and deep cleaning within the skin.

The physical stimulation causes the gastropod to increase the secretions naturally produced by the mucinous, albuminous, and salivary glands. Preferably, the physical stimulus is provided by centrifuging the gastropod. The acceleration during centrifuging causes the snails to increase secretions from the mucinous gland and expel natural secretions from the albuminous and salivary glands.

The process used to obtain the active ingredient involves the steps of: (a) physically stimulating a live gastropod to cause secretion of a fluid, (b) separating the secreted fluid from the live gastropod, (c) centrifuging the secreted fluid, (d) separating the supernatant, (e) filtering the supernatant, and (f) recovering the filtrate. Preferably, the gastropod has been fasted for about 1 to 5 days, 1 to 2 days prior to the physical stimulation. The fasting ensures that there are no toxins present in the secreted fluid. If the gastropod is not fasted, toxins may be present in the secreted fluid; however, conventional means known to those skilled in the art may be used to inactivate the toxins. Fasting avoids toxins that develop from the materials the gastropods eat. One advantage of the present process is that the animals can be used again.

If the active ingredient is to be stored before use, the mixture is rapidly frozen at between about $-10°$ and about $-30°$ C., preferably about $-20°$ C. If large amounts of the active ingredient are to be stored or if the storage time is one year or more, then the mixture is freeze dried. The active ingredient is thermo-sensitive and each glandular secretion is denatured at about $70°$ C. (plus or minus $10°$ C.). If heated to above $90°$ C. the active ingredient's regenerative and antibiotic effects are lost.

The therapeutic and cosmetic compositions comprise an effective amount of the active ingredient and a novel excipient suitable for biologically active ingredients, described hereafter, and other conventional ingredients included in therapeutic and cosmetic compositions provided they do not affect the stability and/or activity of the active ingredient and/or the excipient. Typically, about 0.1 to about 30 to 40%, preferably about 0.5 to about 10%, of the active ingredient is used. The amount of active ingredient used depends upon the intended end use and whether a liquid or freeze-dried active ingredient is used. Generally, the same amount of active ingredient is used whether or not the therapeutic and cosmetic compositions are used for prevention or for treatment.

Preparation of the therapeutic and cosmetic compositions is carried out by mixing the excipient and the active ingredient (unfrozen, if previously frozen) at a temperature below $70°$ C. One of the fundamental effects of the compositions is to protect the skin from injuries. There is no difference in effect due to age, race, or sex in the use of the compositions. The compositions maintain their stability between $-20°$ and $+70°$ C.

Use of the therapeutic composition includes topical application in amounts of about 0.05 to 0.5 $g/cm.^2$, preferably about 0.1 $g./cm.^2$. It can be applied not only to skin but also to mucous membranes such as the respiratory, digestive, urinary, and genital membranes. It can be used for the prevention and/or treatment of radiodermatitis and the prevention of skin cancer caused by exposure to the sun's radiation, as well as for the treatment of all types of burns and injuries including those caused by ionizing radiation, chemical agents such as mustard gas, and thermal agents. It can also be used to treat dermatitis, eczema, diaper rash, and the like; to relieve the itching from insect bites and skin reactions from photosensitivity; to relieve and heal abrasions, chafing, irritation, and chapping; to treat wounds which heal slowly such as episiotomies, laparotomies, and the like; and to treat decubitus, torpidus, and varicose ulcers.

The immediate application of the therapeutic composition eliminates pain and consequently avoids the appearance of primary shock (i.e., nervous system shock), which is statistically responsible for approximately 3% of deaths of burn victims. Applying the composition over burned epidermal surfaces impedes serum loss caused by disturbance to capillary permeability. As a consequence applying the composition avoids the onset of secondary shock, which is statistically responsible for approximately 75% of the deaths in burn victims. After the therapeutic composition is applied the itching, reddening, and pain produced by the burn are decreased and disappear in about 20 minutes and in a few cases up to at most 60 minutes, after application and restoration of the epidermis. The composition has a clear antibiotic effect which prevents infection. It also has an antimicrobial and deodorizing effect. There are no adverse effects. It enhances the action of other drugs such as corticoides and antibiotics so that less is required. When applied to burns in the form of a cream, it acts as a biological coating eliminating the pain from all types of burns without the use of any anesthetic. Use of the cosmetic composition typically includes application in amounts of above 0.01 to 0.06 preferably about 0.03, g./cm.$^2$. It can be used for the repair of any type of injury or damage to the skin. The advantages provided by the use of the cosmetic composition are that it restores, regenerates, and protects the skin. It can be used in facial and hand creams, especially in an anti-wrinkle cream for aging skin and skin on the abdomen or breast where there are stretch marks. It can also be used in moisturizing lotions, toning and cleansing liquids, sunscreen creams, sunscreen tanning creams, deodorants and dentrifices.

DESCRIPTION OF THE PREFERRED EMBODIMENTS

The present invention resulted from observation of the response of a snail to ionizing radiation (X rays or gamma rays) and a study of this biological behavior. Snails perceive radiation, retract their orientation organs, and secrete a large amount of mucous as a defensive response in order to protect themselves. It was hypothesized that they had modified their normal secretion as a means of protection. However, electrophoretic analysis of the secretion shows that it is not different from the mucous normally secreted. This fact, as well as the fact that this animal never suffers from skin infections, directed attention to the possibility of using this secretion as a medication and to the problems involved in obtaining the secretion in sufficient amounts.

The gastropoda whose glandular secretions are used as the active ingredient in the present therapeutic and cosmetic compositions belong to a large group of invertebrate animals ranked as a Class of the *Phylum Mollusca* and represented by such familiar forms as the limpet, the whelk, and the common snail and slug. The shell-less forms are referred to as land or sea slugs, whereas the forms with shells are referred to as land or sea snails. Both Helix and non-Helix forms are suitable. A more extensive discussion of gastropoda may be found in the Encyclopedia Britannica, Vol. 10 at pp. 58–59 (1945); in Invertebrate Zoology: Vol. 1, *Porifera, Cnidaria, Platyhelminthes, Aschelminthes, Mollusca, Annelida,* and Related *Phyla,* Alfred Kaestner, 594 p. (Robt. E. Kireger, Inc., Melbourne, Fla. 1967); and in Invertebrate Zoology (5th Ed.), 864 p. Robert D. Barnes, (Saunders College Publishing, Inc., Troy, Mich., 1987).

Preferred gastropoda include *Helix pomatia, Helix hortensis, Helix nemoralis, Helix cardidula, Helix tchthyomma* (also referred to as *Helix campylea*), *Helix fructicicola* (also referred to as *Helix se uca*), *Helix strigella, Helix fruticum, Helix bidens, Helix arborstorum, Helix rotundata, Helix aculeata, Helix pulchella, Helix personata, Helix holoserica, Helix aperta, Helix parnassia, Helix alonensis, Helix candidissima, Helix pisana,* and *Helix gualteviana.*

The active ingredient is a biological product produced by any type of live gastropod. The technique used to obtain the secreted fluid from the live gastropod does not change the biological structure of the product derived from the gastropod. The secreted fluid does not contain blood, kidney, lung or excrement or muscular contamination when the gastropod is centrifuged.

The method used to produce the active ingredient involves physical stimulus of the gastropod such as that caused by centrifuging. Other suitable, but not preferred, physical stimuli include exposing the gastropod to sound vibrations, low hyperbaric pressure, hypoxic (i.e., oxygenless) conditions, and thermal punctures. Physical stimuli found to be unsuitable include exposure to ionizing radiation and ultrasonic radiation. Extraction of the composition from the gastropod using chemical agents such as hypertonic solutions is not suitable because an insufficient amount of excreted fluid is obtained.

The centrifuging should be carried out under conditions which will not break the shell of the shelled gastropod. The shell protects the heart, and if the shell breaks the heart is punctured and there is an emergence of blood from the heart. If a shell-less gastropod is used, care should be taken in centrifuging the animal so that it remains alive and is not crushed. The centrifuging should be for a time and at a temperature and gravity (G) sufficient to cause the gastropod to secrete fluids. The required number of revolutions per minute (about 2000 to 4000 rpm) will vary depending upon the radius of the arm of the centrifuge. If the radius is large, the acceleration is greater since the circumference is greater. Therefore, the required force is stated as a G force (i.e., the number of times the acceleration of gravity). Preferably, a force of about 1 to 6 G is used for about 2 to about 10 minutes. Most preferably, a force of 2 to 5 G is used. A force of about 7 to 8 G should not be used as it will kill the gastropod. The centrifuging is typically carried out at a temperature of about 10° to 35° C., preferably at about 20° C.

In the preferred method, the centrifuge is accelerated to the desired number of revolutions, decelerated, then accelerated again. This is repeated for the desired number of pulsations. A brake which comes into contact with centrifuge's shaft every few minutes (e.g., 3–4 minutes) is used to provide this pulsation. Typically, the centrifuging is carried out at 2 G for a period of about 10 minutes with 3 or 4 pulsations. After the secreted fluid is separated from the live gastropod, the fluid is centrifuged at about 200 to 5000 rpm for about 2 to 10 minutes. The supernatant is then separated and filtered through a microporous filter having a pore size of about 0.1 to about 1 micron. Filtration can be carried out under pressure to speed up the filtration process.

Any excipient selected for use in the therapeutic and cosmetic compositions should be pharmaceutically and/or cosmetically acceptable and appropriate for the form in which the therapeutic composition will be used, e.g., cream, gel, milk, oil, lotion, and the like. Preferably, the excipient has an affinity for the skin, is well tolerated, and stable and it is used in an amount adequate to provide the desired consistency and ease of application.

An excipient specially designed for the preservation of biological substances and for use in dermatological and cosmetic treatments is used herein. One of the advantages of this excipient is that it will accept almost all other active ingredients and it gives the compositions optimum stability. This preferred excipient is made from a polyethylene glycol mixture having a molecular weight range of about 900–1300, cetyl alcohol, glyceryl monostearate, selected mineral oils, calcium carbonate in micropowder form, zinc oxide in micropowder form, and an aqueous phase. The excipient consists essentially of about 10–17%, preferably 12.0–15.5%, of cetyl alcohol and/or its by-products such as the laurate, myristate, and adipate; about 20–50%, preferably 30–50% of the polyethylene glycol mixture (e.g., a mixture of polyethylene glycol 400, 1500, and 4000); about 3.5–5.8%, preferably 4–6%, of glyceryl monostearate; about 7–12%, preferably 8–10%, of a mineral oil (preferably paraffin oil); about 5–8%, preferably 5.5%–7%, calcium carbonate in the form of a micropowder; about 0.3–0.6%, preferably 0.32–0.40%, zinc oxide in the form of a micropowder; and an effective amount of an aqueous phase, typically up to about 35%, preferably 16–30%. The amount of the aqueous phase should be an amount which is sufficient to give the composition of the desired consistency. If the amount of the aqueous phase is above 35%, a presevative should be used. The aqueous phase consists of water, a saline solution [e.g., a solution of 0.9% sodium chloride which contains no pyrogenous matter], or physiological serum. The percentages are by weight and total 100%. The percentages can be easily adjusted with minimal experimentation to provide the desired creamy consistency. The excipient is odorless and white and unaffected by ultraviolet radiation, x-rays, and gamma rays.

The above excipient is a galenic excipient which is prepared by fusing the cetyl alcohol by a laboratory process, adding the polyethylene glycol mixture, and transferring the mixture to a commercial pharmaceutical laboratory mixer when the fusion point is reached. A second mixture is prepared by fusing the glyceryl monostearate and adding the hot aqueous solution (80° C.). When the second mixture reaches the temperature of the first mixture, the second mixture is added to the mixer. The calcium carbonate and zinc oxide micropowders and the mineral oil are added with continuous stirring. The resulting excipient is white, odorless, and stable. It can be used in the preparation of creams, milks, pomades and the like. It has no detrimental effect, even when used over a long period. It produces no adverse reactions such as allergies or carcinogenic effects. It promotes the absorption of the active ingredient through the skin. It does not break down between −20° and +70° C. is unaffected by humidity, and can be used in many climatic extremes. Also it is not affected by decimeter waves, ultraviolet radiation, gamma radiation of 1.3 MeV, and photons. It is also unaffected by the container in which it is stored. The importance of this excipient is not based on exotic components but on their proportions which is the result of the numerous experimental formulations.

Optional ingredients which can be used in the therapeutic composition for the cases where the aqueous phase is greater than 35% include a preservative such as a methyl paraben, an oxidation inhibitor such as sodium bisulfite, and other ingredients typically included in therapeutic compositions.

Optional ingredients which can be used in the cosmetic composition include mineral oils such as paraffin, turtle, or other oils in amounts of about 1 to about 10%, preferably about 2%; boric acid in amounts of about 0.1 to about 0.6%; preferably about 0.3%; chlorophyll in amounts of about 0.25 to about 1.5%, preferably about 1%; formol (30%) in amounts of about 0.3 to about 3%, preferably about 0.4%; glycerin in amounts of about 0.1 to about 4%, preferably about 0.5%; heparin in amounts of about 0.01 to about 0.4%, preferably about 0.1%; lanolin in amounts of about 0.1 to about 6%, preferably about 0.5%; menthol in amounts of about 0.25 to about 2.5%, preferably about 1%; panthotenic acid in amounts of about 0.01 to about 0.5%, preferably about 0.1%; potassium aluminum sulfate in amounts of about 0.1 to about 1.5%, preferably about 0.4%; copper sulfate in amounts of about 0.01 to about 0.3%, preferably about 0.03%; Vitamin C in amounts of about 0.01 to about 0.5%, preferably about 0.2%; and metallic iodine in amounts of about 0.1 to about 1.1%, preferably about 0.6%. The above percentages are by weight with the weight of the total cosmetic composition being 100%.

Panthotenic acid and heparin are typically used in a nourishing facial cream; glycerin and lanolin are used in a nourishing hand cream; and lanolin and potassium sulfate are used in an anti-wrinkle cream; potassium aluminum sulfate is typically used in a clarifying and moisturizing liquid. Potassium aluminum sulfate is used in a toning and cleansing liquid and, in addition, boric acid and copper sulfate are added. Boric acid, menthol, chlorophyll, and formol (30%) are used in a mild body deodorant but only boric acid is used in a mild intimate deodorant. No optional ingredients are used in the sunscreen cream but metallic iodine and Vitamin C are added to the sunscreen tanning cream.

The activity of the therapeutic composition is evaluated using rats. Both loins of the rat are irradiated with ultraviolet radiation in an amount sufficient to produce an erythma. One loin is treated and the other is not treated and acts as a control. In the same way the rats are irradiated with x-rays using radiotherapy apparatus and the indicated guidelines.

To determine the radioprotective capacity of the composition about 0.1 g./cm$^2$ of the composition is applied to the area to be irradiated and irradiation is carried out at increasing doses. The additional amount of radiation above the typical amount can be given before radiodermatitis occurs is observed. The dose can be increased about 35–45%, provided that the therapeutic composition is applied before irradiation is started and provided that irradiation has never exceeded 1000 cGy without the administration of the therapeutic composition. In cases where it is necessary, customary doses of 5000 to 6000 cGy can be increased to 7000 cGy or much more in a few cases.

One of the advantages of the cosmetic compositions is that it is adaptable to any type of skin and can be used by both sexes. Perfumes without inherent adverse effects can be included in the compositions. When applied, the compositions cause a pleasant sensation. The effectiveness of the cosmetic composition is evaluated by wrinkle reduction and the regeneration of the skin.

It can be appreciated by the practitioner that a large number of variations may be effected in accordance with the procedures described above without materially departing from the scope of the invention. Such variations will be evident to those skilled in the art and are to be included within the scope of the invention.

EXAMPLES

EXAMPLE I

This example describes the preparation of the active ingredient (often referred to as the principal) used in the therapeutic compositions.

A total of 2 kg. of snails (*Helix hortensis*) were fasted for two days and then placed in a 1000 ml. centrifuge tube. The snails were centrifuged at 10°–25° C. for 10 minutes at 2 G. The snails, which were still alive, were removed and 800 g. (800 ml.) of glandular secretion was obtained.

The glandular secretion was centrifuged at 2000 rpm to settle out the large particles. The liquid was decanted off and introduced into a cylinder, the lower end of which contained a milipore filter having a pore size of about 0.1 to about 1 microns. The cylinder was hermetically sealed with a closure bearing a connection to a compressed air system which was used to facilitate the filtration. A total of 600 g. (600 ml.) of filtrate (i.e., the active ingredient) was recovered.

EXAMPLE II

The procedure of Example I was repeated except that a pulsating effect was used to increase the amount of glandular secretion. The centrifugation was carried out by accelerating to 2 G and maintaining that force for 10 minutes, decelerating to 0.5 G and maintaining that force for 20 seconds, and repeating the procedure four times before the centrifuge was stopped and the live snails were removed. A total of 800–900 g. of total glandular extract was obtained by centrifuging 2000 g. of snails. A total of 800 g. (800 ml.) of filtrate (i.e., the active ingredient) was recovered.

EXAMPLE III

While studying the glandular secretions, an elementary purification and fractionation was carried out using a cation exchange resin. The presence of various amino acids, as well as atoxic substances without therapeutic value, was indicated. The principal groups of amino acids included the following:

Group I—amino acids with lateral chains which represented approximately 20 to 30% of the total amino acid content;

Group II—amino acids with hydroxyl (—OH) groups which represented approximately 8 to 10% of the total amino acid content;

Group III—amino acids with thio (—SH) groups in the lateral chain which represented approximately 10 to 13% of the total amino acid content;

Group IV—amino acids with dicarboxylic acid groups which represented approximately 23 to 27% of the total amino acid content;

Group V—amino acids with diamine groups which represented approximately 8 to 12% of the total amino acid content;

Group VI—amino acids with aromatic groups which represented approximately 12 to 16% of the total amino acid content; and Group VII—imino acids which represented approximately 4 to 5% of the total amino acid content.

Group I included about 13.33% isoleucine, about 13.33% leucine, about 13.33% alanine, about 20% valine, and about 40% glycine. Group II included about 30–40% threonine and about 60–70% serine. Group III included about 80–90% cysteine and about 10–20% methionine. Group IV included about 50% each of aspartic acid and glutamic acid. Group V included about 66% arginine and about 33% lysine. Group VI included about 50% each of phenylalanine and tyrosine. Group VII included only proline.

The secretions contained eight of the ten amino acids indispensable for human metabolism and survival. Of this group, only hystidine and tryptofane were not observed.

EXAMPLE IV

This example describes the preparation of an excipient preferred for use in therapeutic compositions containing the active ingredient.

Cetyl alcohol (15 g.) was fused by standard processes and then 50 g. of a mixture of polyethylene glycols [polyethylene glycol 400 (49.%), 1500 (1.0%) and 4000 (49.5%)] was added to form a first mixture. When the fusion point was reached, this mixture was transferred to a commercial pharmaceutical laboratory mixer. A second mixture was prepared by fusing 5 g. of glycerol monostearate and adding 12.6 g. of distilled water or preferably a physiological serum previously heated to 80° C. When the temperature of the second mixture was the same as the temperature of the first mixture, the second mixture was added to the first mixture. With continuous mixing, 7 g. of calcium carbonate and 0.4 g. of zinc oxide, both in the form of micropowders, were incorporated and a small amount of paraffin oil (10 ml.) was added.

EXAMPLE V

This example describes the preparation of a therapeutic cream useful (i) for treating all types of burns including thermal and chemical burns, (ii) for preventing or treating radiodermatitis, and (iii) for preventing or treating sunburn.

A total of 25–30 ml. of the liquid secretion (or 25–30 g. of the freeze-dried secretion) was mixed with 500–600 g. of the excipient of Example IV (i.e., the excipient prepared with a physiological serum) at 30°–40° C. in a mixer. A total of 500–700 g. of cream was obtained.

EXAMPLE VI

This example describes animal experiments using the therapeutic cream of Example V. A control containing only the excipient of Example IV was used.

The previously depilitated backs of rats were irradiated using a single dose of 15,000 cGy with a source to skin distance of 10 cm. using a Phillips RT-100 instrument. After irradiation 1–2 g. per 4.9 cm.$^2$ of the excipient only was applied daily to the control group of 106 rats and the therapeutic cream was applied daily to the test group of 112 rats.

The healing of the radiodermatitis in the rats was observed. The percentage of animals not healed is shown below.

| Week Ended | Animals Untreated | Animals Treated With Excipient Only | Animals Treated With Therapeutic Cream Containing Active Ingredient and Excipient |
| --- | --- | --- | --- |
| 1 | 100% | 100% | 100% |
| 2 | 99% | 90% | 90% |
| 3 | 99% | 85% | 80% |
| 4 | 95% | 80% | 71% |
| 5 | 92% | 77% | 61% |
| 6 | 90% | 76% | 31% |
| 7 | 89% | 75% | 10% |
| 8 | 85% | 75% | 2% |

The results show that the healing provided by the excipient was minimal and probably only due to an insulating effect and that the healing provided by the therapeutic cream was very effective and due to the active ingredient (principal) in the cream.

EXAMPLE VII

This example describes the results of clinical tests in human beings using the therapeutic cream of Example V to protect against radiodermatitis.

The therapeutic cream (0.1 g/10 cm.$^2$) was applied at 24 hour intervals to the skin area to be irradiated. Half the patients were treated with the cream and half were not treated. After irradiation with 1,000 cGy. damage occurred in the untreated patients. In the patients treated with the cream, the protected area was irradiated with up to 7000–8000 cGy before radiodermatitis occurred. This is equivalent to an increased dosage of about 10 to 25%.

In the untreated patients radiodermatitis was observed at about 40–50 Gy (Gy=grey—the unit used to measure radiation). In the treated patients the skin tolerance maximum limit was increased by about 10 gy without the appearance of radiodermatitis. Application of the therapeutic cream was continued for about 30 to 45 days after irradiation was stopped.

EXAMPLE VIII

This example describes the results of clinical tests in human beings using the therapeutic cream of Example V for treatment of radiodermatitis and burns on various areas on the trunk.

The therapeutic cream was applied to the affected area in an amount of 0.1 g/10 cm.$^2$ on a daily basis. The results are shown below.

| Area affected with Radiodermatitis | Mean No Of Days Required To Produce Healing |
| --- | --- |
| mammary fold | 14.4 |
| post-mastectomy scar | 22.9 |
| armpit | 24.5 |
| areas complicated by previous infection | 74.8 |

With radiodermatitis of the mammary fold the drop in the number of cases started on the 17th day. Radiodermatitis was practically eliminated by the 11th day. With radiodermatitis produced on a previous surgical scar, consequent to a mastectomy, the radiodermatitis took much longer to heal. The decrease in the number of ill patients started on the 16th day. About 50% of the patients were healed by the 23rd day. Total healing occurred at the 28th day. The drop in the number of cases with radiodermatitis of the armpit started at the 18th day and radiodermatitis was eliminated by the 28th day.

There was an epithelialization phase which determined the time until the beginning of healing. However, relief of the itch and burning sensation, which in almost all cases did not allow the patient to sleep without pain killers, occurred a few hours after the treatment was begun.

Where the radiodermatitis was complicated and worsened by other processes, the time before reaching the first healings was much longer.

With radiodermatitis of the thorax (79 patients studied) healing rose rapidly between the 19th to 22nd days, reaching a value of 91.1% healed between the 25th and 28th days. After 2.5 weeks the first 25% of the patients were healed. After 3 weeks 50% of the patients were healed. After 4 weeks all patients were healed.

With acute radiodermatitis of the front and rear parts of the abdomen (gluteal area included), in the 21 patients treated, healing started in the 1st week. By the 12th day 50% of the patients were healed and at about the 20th day all the patients were healed.

In the case of radiodermatitis and radiocellulitis, the healing time for the 12 patients was much longer. After the 17th week the very bothersome itching symptom was relieved. Parts of the epidermis and dermis were restored but the appearance of conjunctive injuries caused by skin retraction were still present. The patients had dried up, rough, relatively brittle skin. Therefore, minimal care for several months should be considered.

In the cases of chronic radiodermatitis where the symptoms start 1–15 years after treatment, mass defects cannot be improved except possibly by surgery but relief from itching and/or burning was sometimes achieved by treatment with the therapeutic cream.

Burned skin areas of about 20×20 cm. require about three weeks to healing. Thermal, chemical, and radiodermatitis burns heal in about the same time. The patients do not require analgesics (because they suffer no pain) or antibiotics and they can be treated at home. When a large area of the skin is burned, it is preferred to cover the patient with a sheet impregnated with the cream. For healing sunburns the active ingredient is applied during a period of 3 to 5 days.

EXAMPLE IX

This example describes the preparation of a nourishing facial cream for use on normal, dry, or oily skin.

The cream is prepared by mixing 200 g. of the excipient of Example IV, 10 ml. of the active ingredient, 0.2 g. of panthotenic acid, and 0.2 g. of heparin.

The cream tones and revitalizes the skin. The active ingredient repairs the epithelium and rejuvenates the skin. The cream also serves as an exfoliate, eliminating the outer dead skin layer (epithelial corneal layer) and encouraging the growth of new skin. The use of panthotenic acid and heparin in the cream is optional but preferred because they increase the restorative and penetrating actions.

EXAMPLE X

This example describes the preparation of a nourishing hand cream for use on dry, normal, or oily skin.

The cream is prepared by mixing 100 g. of the excipient of Example IV, 5 g. of the active ingredient, 4 cc. of glycerin, and 0.5 g. of lanolin.

The resulting cream is very smooth and it spreads well. It can be applied in the day or at night to regenerate, rejuvenate, and smooth the skin.

EXAMPLE XI

This example describes the preparation of a clarifying and moisturizing liquid for dry, normal or oily skin.

For use on normal and oily skin, the liquid is prepared by mixing 200 g. of the excipient of Example IV, 20 cc. of the active ingredient, 0.3 g. of potassium aluminum sulfate, and 10 cc. of rosewater.

For use on dry skin, the liquid is prepared as above except that 2 cc. of a mineral oil, e.g., paraffin oil, is added. Colorants may be added but are not preferred because of their possible intolerance and toxicity.

The resulting liquid cleanses and smoothes the skin and heightens the transparency of the complexion. It serves as a base for make-up (e.g., powder). It protects the skin from the harmful action of cosmetic powders which consist of minerals which have a hardness value of 1 on the Mohr scale.

EXAMPLE XII

This example describes the preparation of a toning and cleansing liquid.

The liquid is prepared by mixing 100 g. of the excipient of Example IV, 10 cc. of the active ingredient, 100 cc. of physiological serum, 0.3 g. of potassium aluminum sulfate, 0.5 g. of boric acid, and 0.1 g. of copper sulfate.

The liquid is recommended for use on delicate skin or skin where acne is present. It produces an intense refreshing feeling and a soothing, restful sensation.

EXAMPLE XIII

This example describes the preparation of an anti-wrinkle cream.

A cream for daily use is prepared by mixing 250 g. of the excipient of Example IV, 5 cc. of the active ingredient, 7 g. of lanolin, and 1.56 g. of potassium aluminum sulfate can be added.

A concentrated cream for use no more often than once a week is prepared as above except that 15 g. of the active principal, 15 g. of lanolin, and 2. g. of potassium aluminum sulfate are used.

The cream is easy to apply and is used only on areas where wrinkles exist. The active ingredient is effective in reducing wrinkling, whereas the other components produce an astringent action.

The concentrated cream was tested on more than 200 persons. It was first applied to one half of the face and subsequently to the other half of the face. The effect lasted for approximately one week after each application. The more numerous and larger the wrinkles, the greater was the visible effect of the treatment.

EXAMPLE XIV

This example describes the preparation of a deodorant cream.

A mild body deodorant for use under the armpits and on the feet is prepared by mixing 100 g. of the excipient of Example IV, 10 cc. of the active ingredient, 1 g. of boric acid, 1 g. of menthol, 1 g. of chlorophyll, and 5 cc. of formol (30%).

A mild intimate deodorant for use on the genital area is prepared by mixing 100 g. of the excipient of Example III, 10 cc. of the active ingredient, and 0.5 g. of boric acid.

The resulting deodorant creams are easily applied.

EXAMPLE XV

This example describes the preparation of sunscreen creams. The sun can produce a series of lesions on the skin which are initially precancerous lesions (e.g., seborrheic, keratoses, or actinic keratoses), many of which later become cancers (epitheliomas).

A sunscreen cream is prepared by mixing 250 g. of the excipient of Example IV and 5 cc. of the active ingredient.

A sunscreen tanning cream is prepared as above except that 1 g. of metallic iodine and 0.3 g. of Vitamin C are added.

As a preventative, one thin application of the sunscreen before exposure to the sun is sufficient. If one has suffered a sunburn, a thin coating of the cream should be applied every six hours.

The sunscreen cream was used in the treatment of 306 fair-complexioned persons. The product was used preventively in 6% of the cases and curatively in 94% of the cases. The sunscreen was used in treating persons who suffered sunburns at swimming pools with highly chlorinated water, where the subjects showed blistering (phlytena), and persons who suffered sunburns at beaches. In every case the cream eliminated the pain and burning sensation within seconds of being applied, blisters disappeared in 5 to 6 hours; and the sunburn was gone in 24 hours.

Now that the preferred embodiments of the invention have been described in detail, various modifications and improvements thereon will become readily apparent to those skilled in the art. Accordingly, the spirit and scope of the present invention are to be limited only by the appended claims and not by the foregoing specification.

What is claimed:

1. A method for preparing an active ingredient for use in a therapeutic or cosmetic composition, which comprises the steps of:

a) centrifuging a live Helix gastropod for a time and at a gravity sufficient to cause the gastropod to secrete a fluid containing the active ingredient, but not to kill the grastropod, b) separating the secreted fluid from the live gastropod, c) centrifuging the secreted fluid, d) separating a supernatant, e) filtering the supernatant, and f) recovering at filtrate containing the active ingredient which consists essentially of a mixture of amino acids and non-toxic substances secreted from the mucinous, albuminous, and salivary glands of the live *Helix gastrop*.

2. The method of claim 1, further comprising the step of fasting the live gastropod prior to the step of centrifuging the live gastropod.

3. The method of claim 1, wherein the gastropod is fasted for up to five days and wherein the centrifuging is carried out at about 1 to about 6 G for about 2 to about 10 minutes.

4. The method of claim 3, wherein the gastropod is fasted for about 1 to about 2 days and wherein the centrifuging is carried out in a pulsating manner by successively accelerating and decelerating a centrifuge.

5. The method of claim 2, wherein the fasting is for up to five days.

6. The method of claim 1, wherein the centrifuging of step (a) is carried out in a pulsating manner by successively accelerating and decelerating a centrifuge.

7. The method of claim 1, wherein the filtration of step (f) is carried out using a microparous filter having a pore size of about 0.1 to about 1 micron.

8. The method of claim 7, wherein the filtration is carried out under pressure.

9. The method of claim 1, further comprising the step of freezing the filtrate.

10. The method of claim 1, further comprising the step of freeze-drying the filtrate.

11. The method of claim 1, wherein the centrifuging of step (a) is carried out at less than about 7 to 8 G.

12. The method of claim 11, wherein the centrifuging is carried out at about i to about 6 G for about 2 to about 10 minutes and at about 10° to 35° C.

13. The method of claim 12, wherein the centrifuging is carried out at 2 to 5 G and at about 20° C.

14. The method of claim 1, wherein the centrifuging is carried out in a pulsating manner.

15. The method of claim 14, wherein the pulsating centrifuging is carried out at 2 G for about 10 minutes with 3 or 4 pulsations.

16. The method of claim 1, wherein the *Helix gastropod* is selected from the group consisting of *Helix pomatia, Helix hortensis, Helix nemoralis, Helix cardidula, Helix tchthyomma, Helix fructicicola, Helix strigella, Helix fruticum, Helix bidens, Helix arbostorum, Helix rotundata, Helix aculeata, Helix pulchella, Helix personata, Helix holoserica, Helix aperta, Helix parnassia, Helix alonensis, Helix candidissima, Helix pisana,* and *Helix gualteviana.*

* * * * *